US008967001B2

(12) United States Patent
Zhang

(10) Patent No.: US 8,967,001 B2
(45) Date of Patent: Mar. 3, 2015

(54) TESTING DEVICE AND TESTING SYSTEM FOR TESTING RELIABILITY OF INTERFACE EMPLOYED BY ELECTRONIC DEVICE

(71) Applicants: Fu Tai Hua Industry (Shenzhen) Co., Ltd., Shenzhen (CN); Hon Hai Precision Industry Co., Ltd., New Taipei (TW)

(72) Inventor: Jun-Liang Zhang, Shenzhen (CN)

(73) Assignees: Fu Tai Hua Industry (Shenzhen) Co., Ltd., Shenzhen (CN); Hon Hai Precision Industry Co., Ltd., New Taipei (TW)

( * ) Notice: Subject to any disclaimer, the term of this patent is extended or adjusted under 35 U.S.C. 154(b) by 176 days.

(21) Appl. No.: 13/778,892

(22) Filed: Feb. 27, 2013

(65) Prior Publication Data
US 2013/0220023 A1 Aug. 29, 2013

(30) Foreign Application Priority Data
Feb. 28, 2012 (CN) .......................... 2012 1 0046950

(51) Int. Cl.
*G01N 3/00* (2006.01)
*G01N 19/00* (2006.01)
*G01N 3/32* (2006.01)
*G01R 31/04* (2006.01)
*G01N 3/38* (2006.01)
*G01M 99/00* (2011.01)

(52) U.S. Cl.
CPC .............. *G01N 3/38* (2013.01); *G01M 99/007* (2013.01); *G01R 31/045* (2013.01)
USPC ............ 73/865.3; 73/865.9; 73/808; 324/538

(58) Field of Classification Search
CPC ...... G01M 99/007; G01N 3/38; G01R 31/045
USPC ............ 73/865.3, 865.9, 808, 856, 857, 847, 73/862.322; 324/538
See application file for complete search history.

(56) References Cited

U.S. PATENT DOCUMENTS

| 5,184,517 | A | * | 2/1993 | Kelzer | 73/851 |
|---|---|---|---|---|---|
| 5,447,072 | A | * | 9/1995 | Holung | 73/848 |
| 5,567,884 | A | * | 10/1996 | Dickinson et al. | 73/814 |
| 7,454,980 | B2 | * | 11/2008 | Tan et al. | 73/847 |
| 7,730,791 | B2 | * | 6/2010 | Tan et al. | 73/847 |
| 8,459,126 | B2 | * | 6/2013 | Chen et al. | 73/856 |
| 8,561,487 | B2 | * | 10/2013 | Chen et al. | 73/865.9 |
| 2013/0333480 | A1 | * | 12/2013 | Kessler et al. | 73/788 |

* cited by examiner

*Primary Examiner* — Harshad R Patel
*Assistant Examiner* — Jonathan Dunlap
(74) *Attorney, Agent, or Firm* — Novak Druce Connolly Bove + Quigg LLP

(57) ABSTRACT

An exemplary testing device includes a shell, a motor, a wheel rotating eccentrically, a testing plug, and a sliding assembly. The sliding assembly is configured to move back and forth along a first direction in a first accommodating space of the shell. A periphery of the wheel abuts against two opposite sides of the sliding assembly. An eccentricity e defined between a eccentric hole of the wheel and the center of the wheel causes the sliding assembly to move back and forth along the first direction when the wheel rotates eccentrically. The testing plug connects to the sliding assembly and moves back and forth in unison with the sliding assembly, such that the testing plug can be inserted into the interface of the electronic device more than once.

19 Claims, 4 Drawing Sheets

TESTING DEVICE AND TESTING SYSTEM FOR TESTING RELIABILITY OF INTERFACE EMPLOYED BY ELECTRONIC DEVICE

BACKGROUND

1. Technical Field

The present disclosure generally relates to testing devices and systems, and especially to testing device and system for testing the reliability of an interface employed by an electronic device.

2. Description of Related Art

Most electronic devices include data input/output interfaces and power interfaces for making a connection with other electronic equipment, therefore the reliability of the interfaces directly affects the operational reliability of the electronic devices. An interface testing process is needed in a manufacturing process of the electronic device. In the interface testing process, testers have to manually and repeatedly connect or disconnect test plugs with the interfaces. However, these manual actions are inconvenient and time-consuming for the testers.

What is needed, therefore, is a means which can overcome the described limitations.

BRIEF DESCRIPTION OF THE DRAWINGS

Many aspects of the present embodiments can be better understood with reference to the following drawings. The components in the drawings are not necessarily drawn to scale, the emphasis instead being placed upon clearly illustrating the principles of the present embodiments. Moreover, in the drawings, all the views are schematic, and like reference numerals designate corresponding parts throughout the several views.

DETAILED DESCRIPTION

Reference will be made to the drawings to describe various embodiments.

Figure 1:
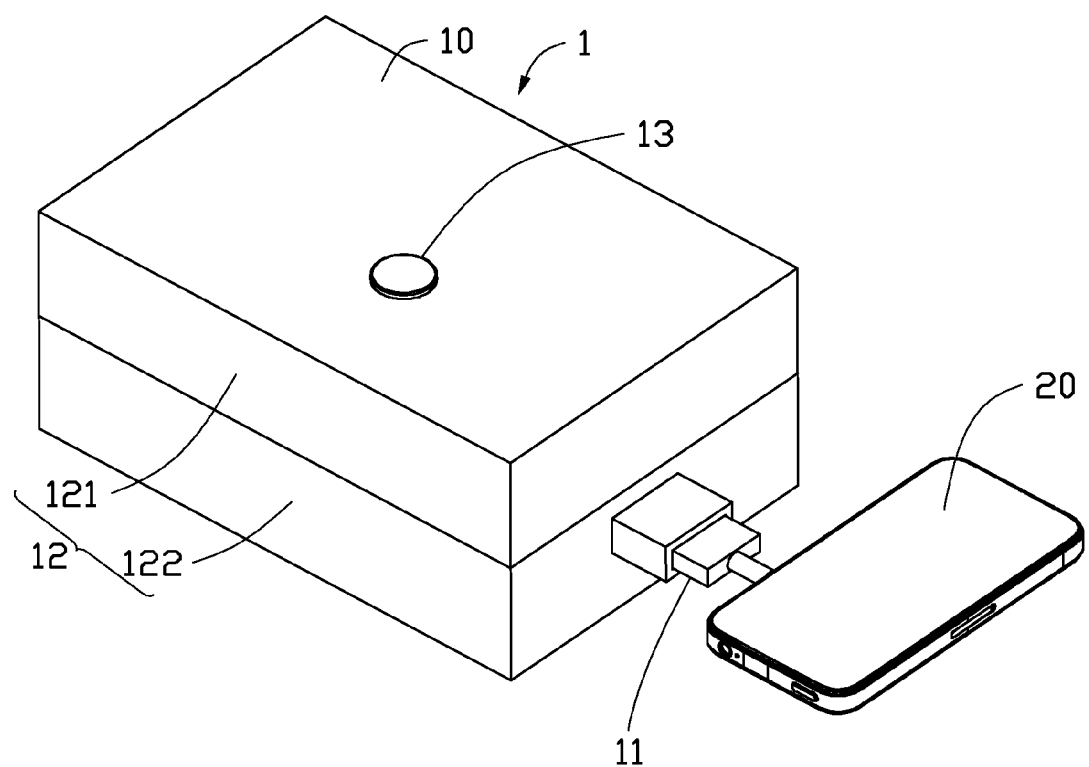
FIG. 1 is an isometric view of an exemplary embodiment of a testing system, wherein the testing system includes an electronic device and a testing device for testing reliability of an interface employed by the electronic device, a testing plug of the testing device being inserted into the interface of the electronic device.

Referring to FIG. 1, a testing system 1 includes an electronic device 20 and a testing device 10 for testing the reliability of an interface employed by the electronic device 20.

Figure 2:
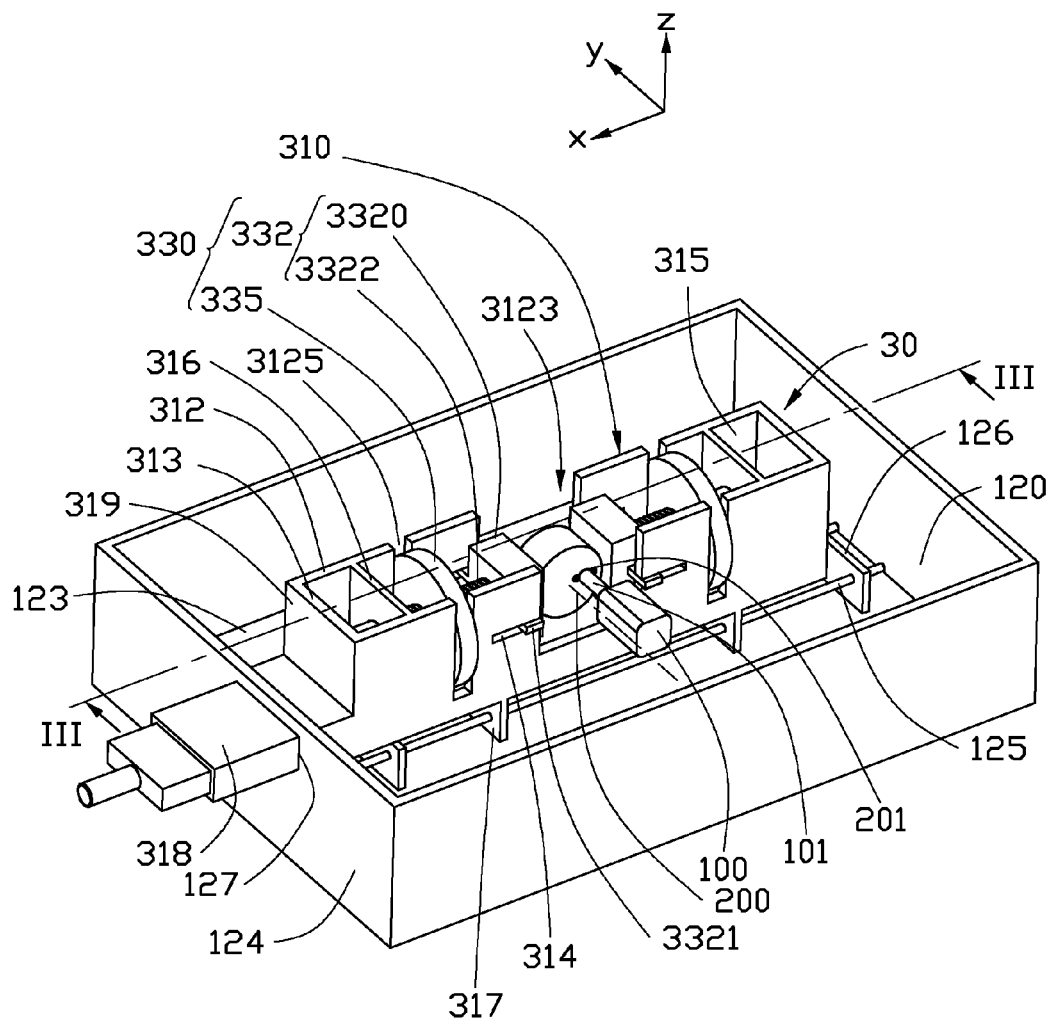
FIG. 2 is an isometric view of the testing device of FIG. 1, showing a bottom cover and a sliding assembly accommodated in the bottom cover, and the top cover removed.

Referring to FIGS. 1 and 2, the testing device 10 includes a shell 12, a sliding assembly 30, a testing plug 11, a switch 13, a motor 100, and an eccentrically-rotating wheel 200. The sliding assembly 30 is received in the shell 12 and moves back and forth along a first direction in the shell 12. In the embodiment, the first direction is a direction parallel to an X-axis as shown in FIG. 2. In the embodiment, the shell 12 includes a top cover 121 and a bottom cover 122. The top cover 121 and the bottom cover 122 engage with each other to define a first accommodating space 120 to receive the sliding assembly 30. An opening (not labeled) is defined in the top cover 121 to allow the switch 13 to be exposed out of the shell 12 via the opening. The motor 100 and the eccentrically-rotating wheel 200 are also received in the receiving space defined by the shell 12.

The bottom cover 122 includes a rectangular bottom plate 123, four sidewalls 124, two supporting plates 126 and two sliding bars 125. The sidewalls 124 extend from an edge of the bottom plate 123 to the top cover 121 and form the first accommodating space 120. One of the sidewalls 124 defines a through hole 127. The two supporting plates 126 are arranged parallel to each other and perpendicularly extend from an inner surface of the bottom plate 123 towards the top cover 121. Two pairs of first fixing holes are defined in the two supporting plates 126 for receiving the two sliding bars 125. Each of the sliding bars 125 extends along the first direction.

The sliding assembly 30 moves back and forth along the two sliding bars 125 and includes a sliding base 310 and two fixing assemblies 330. The sliding base 310 is engaged with the sliding bars 125 and slides back and forth along the sliding bars 125. The two fixing assemblies 330 are arranged at opposite sides of the sliding base 310.

Each fixing assembly 330 includes a fixing screw 332 and an adjusting nut 335. The fixing screw 332 includes a main head 3320, a fixing pole 3322, and two sliding protrusions 3321. The fixing pole 3322 is connected to a surface of the main head 3320 and extends along the first direction. An outer surface of the fixing pole 3322 has threads thereon. The two sliding protrusions 3321 are arranged on two opposite sides of the main head 3320 and each extend along a second direction. The second direction is a direction parallel to a Y-axis as shown in FIG. 2. The adjusting nut 335 has a threaded hole 3350 for the threads of the fixing pole 3322.

The sliding base 310 includes a main portion 319 and a fixing portion 318 connected to the main portion 319 which moves with the main portion 319. An end of the fixing portion 318 extends out of the bottom cover 122 via the through hole 127 and receives the testing plug 11. The main portion 319 includes a base plate 311, two first supporting walls 312, two second supporting walls 313, two flat plates 316 and two connecting plates 317. The base plate 311 is rectangular and substantially parallel to the bottom plate 123. The first supporting walls 312 perpendicularly extend from the two opposite long edges of the base plate 311 and are parallel to the first direction. The second supporting walls 313 perpendicularly extend from the two opposite short edges of the base plate 311 and are parallel to the second direction. The first and second supporting walls 312, 313 and the base plate 311 cooperatively define a second accommodating space 315 therebetween. Each of the first supporting walls 312 defines a first cutout 3123 and two second cutouts 3125 located at opposite sides of the first cutout 3123. Openings of the first and second cutouts 3123, 3125 face towards the top cover 121. Each of the first supporting walls 312 defines two sliding slots 314. The two sliding slots 314 extend along the first direction, and are located at the opposite side-surfaces of the first cutout 3123. The two sliding slots 314 communicate with the first cutout 3123. Each of the flat plates 316 perpendicularly extends from the base plate 311, and interconnects the two first supporting walls 312. Each of the flat plates 316 is parallel to the second supporting wall 313, and located between a corresponding second supporting wall 313 and a corresponding second cutout 3125. Each of the flat plates 316 defines a hole corresponding to the threaded hole 3350 of the adjusting nut 335. The two connecting plates 317 extend downward from the base plate 311, and are located outside the second accommodating space 315. Each connecting plate 317 defines two second fixing holes (not labeled) to receive the two sliding bars 125.

The motor 100 is electrically connected to the switch 13. The motor 100 includes a spindle 101 extending along the second direction. The spindle 101 is driven to rotate by the motor 100. The motor 100 is fixed in the first accommodating space 120 and corresponds to the first cutout 3123, with the spindle 101 extending into the second accommodating space 315 through the first cutout 3123.

The eccentrically-rotating wheel 200 is circular, and defines at least one eccentric hole 201. In this embodiment, the eccentrically-rotating wheel 200 defines three eccentric holes 201 on a single radius of the eccentrically-rotating wheel 200. An eccentricity e is defined between every eccentric hole 201 and a center 202 of the eccentrically-rotating wheel 200.

In assembly of the testing device 10, the main portion 319 is located in the first accommodating space 120, with the fixing portion 318 of the sliding base 310 extending out of the through hole 127 of the bottom cover 122. The testing plug 11 is fixed to the fixing portion 318. The connecting plates 317 of the sliding base 310 are located between the supporting plates 126 of the bottom cover 122, the second fixing holes of the connecting plates 317 align with the first fixing holes of the supporting plates 126, the sliding bars 125 are inserted into the first and second fixing holes, and ends of the sliding bars 125 are screwed to the supporting plates 126 to prevent any movement of the sliding bars 125. The sliding base 310 moves back and forth along the sliding bar 125.

The adjusting nuts 335 are inserted into and are captive within the second cutouts 3125 of the sliding base 310. The fixing poles 3322 of the fixing screws 332 are inserted into the threaded holes 3350 of the adjusting nuts 335 and the holes of the flat plates 316 by rotation of the adjusting nuts 335, and the sliding protrusions 3321 of the fixing screws 332 are received in the sliding slots 3125 of the first supporting walls 312. The distance between the two main heads 3320 of the two fixing screws 332 is adjustable by rotating the adjusting nuts 335. When the distance between the two main heads 3320 is greater than the diameter of the eccentrically-rotating wheel 200, the eccentrically-rotating wheel 200 is positioned within the first cutout 3123 and between the two main heads 3320, and the spindle 101 of the motor 100 extends into the first cutout 3123 for insertion into one of the eccentric holes 201 of the eccentrically-rotating wheel 200.

Figure 3:
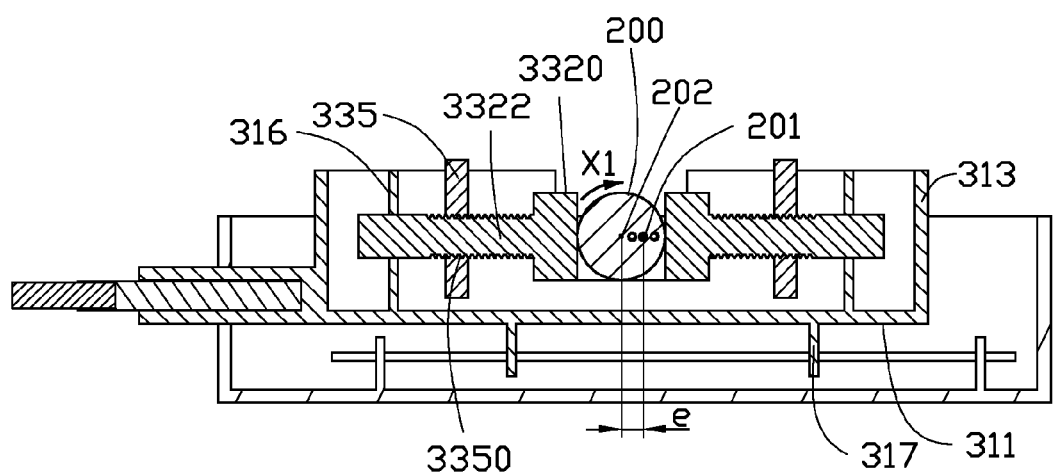
FIG. 3 is a cross-sectional view of the testing device of FIG. 2, taken along line thereof, showing the sliding assembly moving forward.
Figure 4:
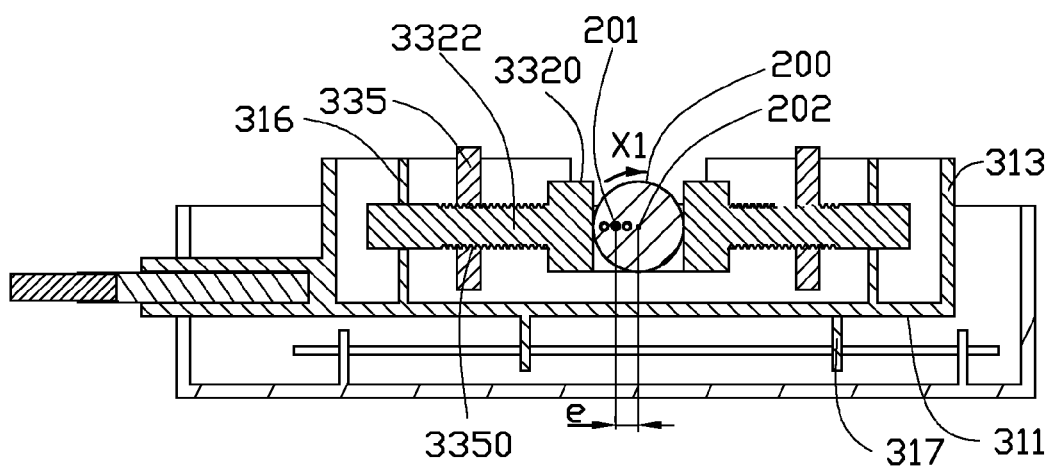
FIG. 4 is similar to FIG. 3, but showing the sliding assembly moving backward.

The distance between the two main heads 3320 is adjusted by rotating the adjusting nuts 335, so as to make the two main heads 3320 abut against opposite sides of a periphery of the eccentrically-rotating wheel 200. Because the motor 100 is fixed in the first accommodating space 120, and the spindle 101 is inserted and fixed in the eccentric hole 201, the sliding base 310 is fixed in the first accommodating space 120 when the motor 100 is turned off. The eccentricity e defined between the eccentric hole 201 and the center 202 of the eccentrically-rotating wheel 200 causes the sliding base 310 to move back and forth along the sliding bar 125 when the eccentrically-rotating wheel 200 rotates around the spindle 101. When the point of contact between the main head 3320 of the fixing screw 332 adjacent to the fixing portion 318 and the eccentrically-rotating wheel 200 is farthest from the spindle 101, the length of the fixing portion 318 protruding out from the bottom cover 122 is at the maximum (see FIG. 3). When the point of contact between the main head 3320 of the fixing screw 332 adjacent to the fixing portion 318 and the eccentrically-rotating wheel 200 is nearest the spindle 101, the length of the fixing portion 318 protruding out from the bottom cover 122 is at the minimum (see FIG. 4).

When the testing device 10 is used, the electronic device is set in front of the testing plug 11, and the testing plug 11 is arranged to correspond to the interface of the electronic device 20. The motor 100 is turned on by the switch 13 so as to drive the spindle 101 to rotate, and the rotation of the eccentrically-rotating wheel 200 forces the sliding base 310 to move back and forth along the sliding bar 125. When the length of the fixing portion 318 of the sliding base 310 protruding out of the bottom cover 122 is at maximum, the testing plug 11 is completely inserted into the interface of the electronic device 20, and when the length of the fixing portion 318 of the sliding base 310 protruding out of the bottom cover 122 is at minimum, the testing plug 22 is extracted from the interface of the electronic device 20. Repeated connection and disconnection cycles of the testing plug with the interface of the electronic device 20 takes place as long as the eccentrically-rotating wheel 200 is rotated, and when the number of connection and disconnection cycles is sufficient for the interface testing of the electronic device 20, the motor 100 can be turned off by the switch 13.

With the above-described configuration, the tester can use the testing device 10 for the interface testing, the user only needs to turn on the testing device 10 via the switch 13, and turn it off when finished.

It is believed that the present embodiments and their advantages will be understood from the foregoing description, and it will be apparent that various changes may be made thereto without departing from the spirit and scope of the description or sacrificing all of their material advantages, the examples hereinbefore described merely being exemplary embodiments.

What is claimed is:

1. A testing device, comprising:
    a shell defining a through hole and a first accommodating space, the through hole interconnects the accommodating space and the outside of the shell;
    a motor fixed in the first accommodating space;
    an eccentrically-rotating wheel defining at least one eccentric hole, an eccentricity e defined between the center of the eccentrically-rotating wheel and each of the at least one eccentric hole, and the motor configured to drive the eccentrically-rotating wheel to rotate around one of the at least one eccentric hole;
    a sliding assembly configured to move back and forth along a first direction in the first accommodating space, the sliding assembly comprising a fixing portion, and an end of the fixing portion extended out of the shell via the through hole; and
    a testing plug fixed to the end of fixing portion of the sliding assembly extended out of the shell, a periphery of the eccentrically-rotating wheel abutting against two opposite sides of the sliding assembly, wherein the eccentricity e defined between the one of the at least one eccentric hole and the center of the eccentrically-rotating wheel causes the sliding assembly to move back and forth along the first direction when the eccentrically-rotating wheel rotates, and the testing plug moves back and forth in unison with the fixing portion of the sliding assembly, thereby repeatedly connecting and disconnecting the testing plug with interfaces of an electronic device.

2. The testing device of claim 1, wherein the motor comprising a spindle, the motor is configured to drive the spindle to rotate, the spindle is inserted and fixed in the one of the at least one eccentric hole, and the eccentrically-rotating wheel rotates in unison with the spindle.

3. The testing device of claim 2, wherein one of the two sides abutting against the periphery of the eccentrically-rotating wheel is adjacent to the fixing portion of the sliding assembly, and the other side of the two sides is away from the fixing portion, when a point of contact between the side of the sliding assembly adjacent to the fixing portion rotates farthest from the spindle, the length of the fixing portion protruding out from the shell is at the maximum, and when the point of contact between the side of the sliding assembly adjacent to the fixing portion rotates nearest the spindle, the length of the fixing portion protruding out from the shell is at the minimum.

4. The testing device of claim 3, wherein the sliding assembly comprises a sliding base and two fixing assemblies arranged at opposite sides of the sliding base, each fixing assembly comprises a fixing screw and an adjusting nut, the fixing screw comprises a main head and a fixing pole with threads, the adjusting nut defines a threaded hole for the threads of the fixing pole, the adjusting nuts of the two fixing assemblies are rotatably fixed to the sliding base at two opposite sides of the eccentrically-rotating wheel, the two fixing screws are located at two opposite sides of the eccentrically-rotating wheel with the fixing poles inserted into the threaded holes of the adjusting nuts, and the two main heads of the fixing screws abut against the periphery of the eccentrically-rotating wheel.

5. The testing device of claim 4, wherein the sliding base comprises a main portion with the fixing portion connected to the main portion, the main portion comprises a base plate, two first supporting walls, and two second supporting walls, the base plate is rectangular, the first supporting walls are parallel to the first direction and perpendicularly extend from two opposite sides of the base plate, the second supporting walls are parallel to a second direction and perpendicularly extend from the other two opposite sides of the base plate, the second direction is perpendicular to the first direction, and the first and second supporting walls and the base plate cooperatively define a second accommodating space therebetween.

6. The testing device of claim 5, wherein each of the first supporting walls defines a first cutout and two second cutouts located at two opposite sides of the first cutout, the first cutout corresponds to the eccentrically-rotating wheel, the two adjusting nuts are inserted into and captive within the second cutouts, the adjusting nuts are parallel to the second supporting walls, and the fixing portion is located outside the second accommodating space and connected to one of the second supporting walls.

7. The testing device of claim 6, wherein the shell comprises a top cover and a bottom cover, the bottom cover comprises a rectangular bottom plate and four sidewalls extended from an edge of the bottom plate to the top cover, the bottom plate and the sidewalls define the first accommodating space, and one of the sidewalls defines the through hole, two supporting plates perpendicularly extend from an inner surface of the bottom plate towards the top cover, and each supporting plate defines a pair of the first fixing holes, two connecting plates perpendicularly extend from the base plate of the sliding base towards the bottom plate of the bottom cover, and the two connecting plates locate between the two supporting plates, each of the connecting plates defines a pair of the second fixing holes aligned with the pair of the first fixing holes to receive two sliding bars, each of the sliding bars extends along the first direction, and the sliding assembly moves back and forth along the sliding bars.

8. The testing device of claim 7, wherein openings of the first and second cutouts face the top cover, each of the first supporting walls defines two sliding slots, the two sliding slots extend along the first direction, and locate at two opposite side-surfaces of the first cutout, and the two sliding slots communicate with the first cutout, two sliding protrusions are connected to two opposite sides of each main head of the fixing screw, the sliding protrusions are received in the sliding slots, and configured to move back and forth in the sliding slots.

9. The testing device of claim 7, wherein the top cover defines an opening to receive a switch which is electrically connected to the motor, the switch is configured to turn on and turn off the motor.

10. A testing system, comprising:
an electronic device comprising at least one interface; and
a testing device comprising:
a shell defining a through hole and a first accommodating space, the through hole interconnects the accommodating space and the outside of the shell;
a motor fixed in the first accommodating space;
an eccentrically-rotating wheel defining at least one eccentric hole, an eccentricity e defined between the center of the eccentrically-rotating wheel and each of the at least one eccentric hole, and the motor configured to drive the eccentrically-rotating wheel to rotate around one of the at least one eccentric hole;
a sliding assembly configured to move back and forth along a first direction in the first accommodating space, the sliding assembly comprising a fixing portion, and an end of the fixing portion protruded out of the shell from the through hole; and
a testing plug fixed to the end of the fixing portion of the sliding assembly protruded out of the shell, a periphery of the eccentrically-rotating wheel abutting against two opposite sides of the sliding assembly, wherein the eccentricity e defined between the one of the at least one eccentric hole and the center of the eccentrically-rotating wheel causes the sliding assembly to move back and forth along the first direction when the eccentrically-rotating wheel rotates, the testing plug move back and forth in unison with and the fixing portion of the sliding assembly, and the testing plug is capable of inserted into the at least one of the interface of the electronic device more than once.

11. The testing system of claim 10, wherein the motor comprising a spindle, the motor is configured to drive the spindle to rotate, the spindle is inserted and fixed in the one of the at least one eccentric hole, and the eccentrically-rotating wheel rotates in unison with the spindle.

12. The testing system of claim 11, wherein one of the two sides abutting against the periphery of the eccentrically-rotating wheel is adjacent to the fixing portion of the sliding assembly, and the other side of the two sides is away from the fixing portion, when a point of contact between the side of the sliding assembly adjacent to the fixing portion rotates farthest from the spindle, the length of the fixing portion protruding out from the shell is at the maximum, and when the point of contact between the side of the sliding assembly adjacent to the fixing portion rotates nearest the spindle, the length of the fixing portion protruding out from the shell is at the minimum.

13. The testing system of claim 12, wherein the sliding assembly comprises a sliding base and two fixing assemblies arranged at opposite sides of the sliding base, each fixing assembly comprises a fixing screw and an adjusting nut, the fixing screw comprises a main head and a fixing pole with threads, the adjusting nut defines a threaded hole for the threads of the fixing pole, the adjusting nuts of the two fixing assemblies are rotatably fixed to the sliding base at two opposite sides of the eccentrically-rotating wheel, the two fixing screws are located at two opposite sides of the eccentrically-rotating wheel with the fixing poles of the fixing screws inserted into the threaded holes of the adjusting nuts, and the two main heads of the fixing screws abut against the periphery of the eccentrically-rotating wheel.

14. The testing system of claim 13, wherein the sliding base comprises a main portion with the fixing portion connected to the main portion, the main portion comprises a base plate, two first supporting walls, and two second supporting walls, the base plate is rectangular, the first supporting walls are parallel to the first direction and perpendicularly extend from two opposite sides of the base plate, the second supporting walls are parallel to a second direction and perpendicularly extend from the other two opposite sides of the base plate, the second direction is perpendicular to the first direction, and the first and second supporting walls and the base plate cooperatively define a second accommodating space therebetween.

15. The testing system of claim 14, wherein each of the first supporting walls defines a first cutout and two second cutouts located at two opposite sides of the first cutout, the first cutout corresponds to the eccentrically-rotating wheel, the two adjusting nuts are inserted into and captive within in the second cutouts, the adjusting nuts are parallel to the second supporting walls, and the fixing portion is located outside the second accommodating space and connected to one of the second supporting walls.

16. The testing system of claim 15, wherein the shell comprises a top cover and a bottom cover, the bottom cover comprises a rectangular bottom plate and four sidewalls extended from an edge of the bottom plate to the top cover, the bottom plate and the sidewalls define the first accommodating space, and one of the sidewalls defines the through hole, two supporting plates perpendicularly extend from an inner surface of the bottom plate towards the top cover, and each supporting plate defines a pair of the first fixing holes, two connecting plates perpendicularly extend from the base plate of the sliding base towards the bottom plate of the bottom cover, and the two connecting plates locate between the two supporting plates, each of the connecting plates defines a pair of the second fixing holes aligned with the pair of the first fixing holes to receive two sliding bars, each of the sliding bars extends along the first direction, and the sliding assembly moves back and forth along the sliding bars.

17. The testing system of claim 16, wherein openings of the first and second cutouts face the top cover, each of the first supporting walls defines two sliding slots, the two sliding slots extend along the first direction, and locate at two opposite side-surfaces of the first cutout, and the two sliding slots communicate with the first cutout, two sliding protrusions are connected to two opposite sides of each main head of the fixing screw, the sliding protrusions are received in the sliding slots, and configured to move back and forth in the sliding slots.

18. The testing system of claim 16, wherein the top cover defines an opening to receive a switch which is electrically connected to the motor, the switch is configured to turn on and turn off the motor.

19. The testing system of claim 17, wherein when switch drives the motor to turn on, the motor drives the spindle and the eccentrically-rotating wheel to rotate, and the sliding base moves back and forth along the sliding bar when the eccentrically-rotating wheel rotates, when the length of the fixing portion of the sliding base protruding out of the bottom cover is at maximum, the testing plug is completely inserted into the interface of the electronic device, and when the length of the fixing portion of the sliding base protruding out of the bottom cover is at minimum, the testing plug is extracted from the interface of the electronic device, repeated connection and disconnection cycles of the testing plug with the interface of the electronic device takes place as long as the eccentrically-rotating wheel is rotated, and when the number of the connection and disconnection cycles is sufficient for the interface testing of the electronic device, the motor can be turned off by the switch.

* * * * *